United States Patent [19]

Alvarez et al.

[11] Patent Number: 5,523,289

[45] Date of Patent: Jun. 4, 1996

[54] PHARMACEUTICAL COMPOSITION

[75] Inventors: Francisco J. Alvarez, Lindenhurst; Kathy M. O'Connor, Round Lake Beach, both of Ill.

[73] Assignee: Abbott Laboratories, Abbott Park, Ill.

[21] Appl. No.: 78,807

[22] Filed: Jun. 17, 1993

Related U.S. Application Data

[63] Continuation of Ser. No. 780,664, Oct. 18, 1991, abandoned, which is a continuation-in-part of Ser. No. 683,663, Apr. 15, 1991, abandoned.

[51] Int. Cl.[6] ............... A61K 31/195; A61K 31/19; A61K 38/00
[52] U.S. Cl. ............... 514/19; 514/252; 514/574
[58] Field of Search .................. 424/464, 465, 424/468, 469, 470, 480; 514/218, 227.5, 231.2, 238.8, 574, 19, 252

[56] References Cited

U.S. PATENT DOCUMENTS

| | | | |
|---|---|---|---|
| 4,650,664 | 3/1987 | Schepky et al. | 424/456 |
| 4,724,148 | 2/1988 | Sonobe et al. | 424/480 |
| 4,826,815 | 5/1989 | Lucy et al. | 514/19 |
| 4,826,958 | 5/1989 | Sham | 530/331 |
| 4,857,507 | 8/1989 | Rosenberg et al. | 514/18 |
| 5,284,849 | 2/1994 | Rosenberg et al. | 514/252 |

FOREIGN PATENT DOCUMENTS

| | | |
|---|---|---|
| 361354 | 4/1990 | European Pat. Off. |
| 3240336 | 5/1988 | Germany . |
| 60-023326 | 2/1985 | Japan . |
| 60-163823 | 8/1985 | Japan . |
| 3086834 | 4/1991 | Japan . |

*Primary Examiner*—Marianne M. Cintins
*Assistant Examiner*—Kevin E. Weddington
*Attorney, Agent, or Firm*—Steven R. Crowley; Michael J. Ward

[57] ABSTRACT

A pharmaceutical tablet composition comprising a compound of the formula (II):

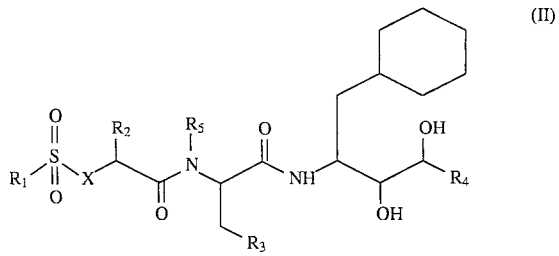

wherein $R_1$ is 4-piperazinyl, 1-methyl-4-piperazinyl, 1-methyl-1-oxo-4-piperazinyl, 2-oxo-4-piperazinyl, 4-morpholinyl, 4-thiomorpholinyl or 1-methyl-4-homopiperazinyl;

$R_2$ is benzyl, p-methoxybenzyl, 2-phenylethyl, 1-naphthylmethyl or 2-naphthylmethyl;

$R_3$ is 4-thiazolyl, 2-amino-4-thiazolyl, 2-thiazolyl, 5-thiazolyl, 1-pyrazolyl, 3-pyrazolyl, 1-imidazolyl, n-propyl, isopropyl, $CH_3S-$ or $CH_3SCH_2-$;

$R_4$ is loweralkyl or cyclopropyl;

$R_5$ is hydrogen or loweralkyl; and

X is $CH_2$ or NH;

or a pharmaceutically acceptable salt, ester or prodrug thereof, and a pharmaceutically acceptable organic polycarboxylic acid. In addition, the tablet composition can further comprise one or more pharmaceutically acceptable non-ionic surfactants.

6 Claims, No Drawings

PHARMACEUTICAL COMPOSITION

This is a continuation of U.S. patent application Ser. No. 07/780,664, filed Oct. 18, 1991, which is now abandoned which is a continuation-in-part of Ser. No. 07/683,663 filed Apr. 15, 1991, now abandoned.

TECHNICAL FIELD

A pharmaceutical composition is disclosed for peptidomimetic compounds which are inhibitors of renin. In particular, the composition comprises a tablet comprising the renin inhibitor and a pharmaceutically acceptable organic polycarboxylic acid. The tablet can also comprise one or more pharmaceutically acceptable non-ionic surfactants.

BACKGROUND OF THE INVENTION

The ability to orally administer peptide or peptide-like therapeutic agents has been a long-standing goal of pharmaceutical research. For example, many efforts have been made to develop an oral dosage form for insulin. Unfortunately, these efforts have been unsuccessful.

Properties which make peptides difficult to administer orally include their susceptibility to enzymatic degradation in the digestive tract and the fact that some peptides are not readily transported from the digestive system into the blood stream. As a result of these problems, it is difficult to achieve desired blood levels of peptides or peptide-like therapeutic agents with relatively low oral doses and a relatively low number of oral doses per day.

Methods used to overcome the ability of peptides to be enzymatically degraded and to improve absorption into the blood stream from the digestive tract have included making analogs which are less peptide-like in structure and which are reduced in size (i.e., molecular weight). Such methods are deemed to be successful when the peptide analog achieves satisfactory blood levels after oral administration.

The above-mentioned techniques have been applied to preparing analogs of the peptide substrate of the enzyme renin. Small, peptide-like molecules have been prepared which show efficacy in lowering blood pressure. For example, compound I (shown below) reduces blood pressure in salt depleted dogs after oral or intravenous administration. However, the bioavailability on oral dosing (to fasted dogs) of salts of compound I as a standard tablet or powder filled capsule compositions (see Example 12, compositions S1-S5) is about 9 to 44%. To be able to administer the compound at the lowest possible dose and lowest frequency of dosing, it would be preferrable if the oral bioavailability of compound I and its pharmaceutically acceptable salts was higher than that exhibited by the conventional tablets and powder filled capsules mentioned above.

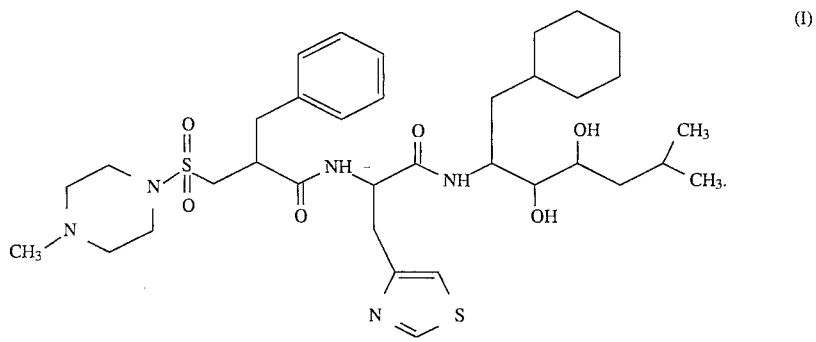

(I)

DISCLOSURE OF THE INVENTION

In accordance with the present invention there is a pharmaceutical tablet composition comprising a compound of the formula (II):

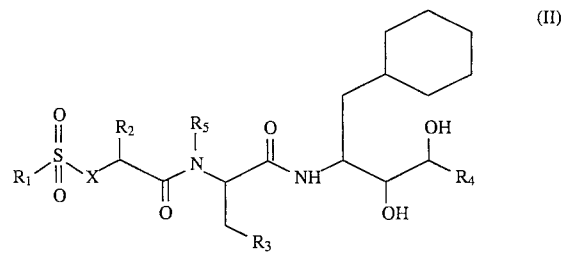

(II)

wherein $R_1$ is 4-piperazinyl, 1-methyl-4-piperazinyl, 1-methyl-1-oxo-4-piperazinyl, 2-oxo-4-piperazinyl, 4-morpholinyl, 4-thiomorpholinyl or 1-methyl-4-homopiperazinyl;

$R_2$ is benzyl, p-methoxybenzyl, 2-phenylethyl, 1-naphthylmethyl or 2-naphthylmethyl;

$R_3$ is 4-thiazolyl, 2-amino-4-thiazolyl, 2-thiazolyl, 5-thiazolyl, 1-pyrazolyl, 3-pyrazolyl, 1-imidazolyl, n-propyl, isopropyl, $CH_3S$— or $CH_3SCH_2$—;

R4 is loweralkyl or cyclopropyl;

$R_5$ is hydrogen or loweralkyl; and

X is $CH_2$ or NH; or a pharmaceutically acceptable salt, ester or prodrug thereof, and a pharmaceutically acceptable organic polycarboxylic acid. In addition, the tablet composition can further comprise one or more pharmaceutically acceptable non-ionic surfactants. When formulated as a tablet comprising a pharmaceutically acceptable organic polycarboxylic acid or a pharmaceutically acceptable organic polycarboxylic acid and one or more pharmaceutically acceptable non-ionic surfactants, the compound of formula (II)

demonstrates improved oral bioavailability when compared to the same compound administered as a conventional tablet or powder filled capsule composition.

The term "pharmaceutically acceptable organic polycarboxylic acid" as used herein refers to organic compounds having two or more carboxylic acid substituents, such as citric acid, malonic acid, succinic acid, tartaric acid, fumaric acid, maleic acid, malic acid, adipic acid, glutaric acid or oxalic acid and the like. Preferably, the organic polycarboxylic acid has a pKa lower than about 4.0.

The term "pharmaceutically acceptable non-ionic surfactant" as used herein refers to mono fatty acid esters of poyoxyethylene (20) sorbitan (for example, Tween® 20 (polyoxyethylene (20) sorbitan monolaurate), Tween® 40 (polyoxyethylene (20) sorbitan monopalmitate), Tween® 80 (polyoxyethylene (20) sorbitan monooleate) and the like), ethers of polyoxyethylene (for example, Brij® 30 (polyoxyethylene (4) lauryl ether), Brij® 35 (polyoxyethylene (23) lauryl ether), Brij® 58 (polyoxyethylene (20) cetyl ether), Brij® 78 (polyoxyethylene (20) stearyl ether), Brij® 99 (polyoxyethylene (20) oleyl ether) and the like), block copolymers of ethylene oxide and propylene oxide (for example, Pluronic® L101, Pluronic® L31, Pluronic® L61, Pluronic® L72, Pluronic® L92 and the like), and ethoxylated fatty acids (for example, Emulphor® CO 5 and Emulphor® CO-25 (ethoxylated castor oil), Emulphor® MA-8, Emulphor® VN 610 and Emulphor® MS 8, Emulphor® COH 25 (ethoxylated hydrogenated castor oil) and the like).

The pharmaceutical tablet composition of the invention can also comprise excipients such as fillers (for example, microcystalline cellulose (Avicel®), starch, pregelatinized starch, lactose or dicalcium phosphate and the like), disintegrants (for example, crospovidone, croscarmellose sodium, pregelatinized starch or sodium starch glycolate and the like), lubricants (for example, magnesium stearate, stearic acid, hydrogenated vegetable oils (for example, Sterotex® K), talc or colloidal silica and the like) and binders (for example, polyvinylpyrrolidone (povidone) or Klucel and the like).

The pharmaceutical tablet composition of the invention can further comprise various additives such as antioxidants (for example, butylated hydroxyanisole (BHA), butylated hydroxytoluene (BHT) or tocopherol acetate (vitamin E) and the like), flavoring agents and coloring agents.

A typical tablet composition of the invention comprises a compound of formula II at a concentration of up to about 35 weight %, preferably from about 4.0 to about 30 weight %, a pharmaceutically acceptable organic polycarboxylic acid (from about 1 weight % to about 20 weight %, preferably from about 3.0 to about 15 weight %), a filler (from about 30.0 weight % to about 90.0 weight %, preferably from about 40.0 to about 85.0 weight %) and, optionally, one or more pharmaceutically acceptable non-ionic surfactants (totalling from about 0 weight % to about 10.0 weight %, preferrably from about 0.3 to about 3.0 weight %).

A preferred tablet composition of the invention comprises a compound of the formula (II) at a concentration of from about 4.0 weight % to about 30.0 weight %, citric acid (from about 3.0 weight % to about 5.0 weight %) and Avicel® (from about 40.0 weight % to about 80.0 weight %).

Another preferred composition of the invention comprises a compound of formula (II) at a concentration of from about 4.0 weight % to about 30.0 weight %, citric acid (from about 3.0 weight % to about 5.0 weight %), one or more pharmaceutically acceptable non-ionic surfactants (totalling from about 1.0 weight % to about 2.0 weight %) and Avicel® (from about 40.0 weight % to about 80.0 weight %).

Another preferred composition of the invention comprises a compound of formula (III) or a pharmaceutically acceptable salt, ester or prodrug thereof at a concentration of from about 4.0 weight % to about 30.0 weight %, citric acid (from about 3.0 weight % to about 5.0 weight %) and Avicel® (from about 40.0 weight % to about 80.0 weight %).

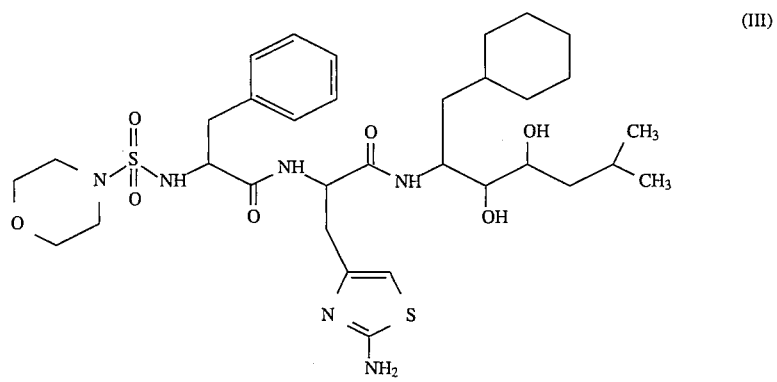

(III)

A most preferred composition of the invention comprises a compound of formula I or III or a pharmaceutically acceptable salt, ester or prodrug thereof at a concentration of from about 4.0 weight % to about 30.0 weight % citric acid (from about 3 0 weight % to about 5.0 weight %), Avicel® (from about 40.0 weight % to about 80.0 weight %), crospovidone (from about 2.0 weight % to about 4.0 weight %), croscarmellose sodium (from about 2.0 weight % to about 4.0 weight %) and magnesium stearate (from about 0.5 weight % to about 1.5 weight %).

The compounds of formula I, II and III contain two or more asymmetric carbon atoms and thus can exist as pure diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13–30.

The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "halogen" or "halide" as used herein refers to F, Cl, Br or I.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The terms "alkoxy" and "thioalkoxy" as used herein refer to $R_{30}O—$ and $R_{30}S—$, respectively, wherein $R_{30}$ is a loweralkyl group or benzyl.

The term "haloalkoxy" as used herein refers to $R_{31}O—$ wherein $R_{31}$ is a haloalkyl group.

The term "aminocarbonyl" as used herein refers to $—C(O)NH_2$.

The term "alkylaminocarbonyl" as used herein refers to $—C(O)NHR_{32}$ wherein $R_{32}$ is loweralkyl.

The term "dialkylaminocarbonyl" as used herein refers to $—C(O)NR_{33}R_{34}$ wherein $R_{33}$ and $R_{34}$ are independently selected from loweralkyl.

The term "alkoxycarbonyl" as used herein refers to $—C(O)OR_{35}$ wherein $R_{35}$ is loweralkyl.

The compounds of formula I, II or III can be used in the form of pharmaceutically acceptable salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate (mesylate), nicotinate, 2-naphthalenesulfonate, oxalate, pamoate, pectinate, persulfate, phosphate, 3-phenylpropionate, picrate, pivalate, propionate, succinate, tartrate, thiocyanate, tosylate, and undecanoate.

Examples of acids which may be employed to form pharmaceutically acceptable acid addition salts include such inorganic acids such as hydrochloric acid, sulphuric acid and phosphoric acid and such organic acids as oxalic acid, maleic acid, succinic acid, methanesulfonic acid and citric acid.

The compounds of the present invention can also be used in the form of prodrugs which include esters. Examples of such esters include a hydroxyl-substituted compound of formula (II) which has been acylated with a blocked or unblocked amino acid residue, a phosphate function, or a hemisuccinate residue. The amino acid esters of particular interest are glycine and lysine; however, other amino acid residues can also be used. These esters serve as prodrugs of the compounds of the present invention and serve to increase the solubility of these substances in the gastrointestinal tract. The prodrugs are metabolically converted in vivo to the parent compound of formula (II). The preparation of the pro-drug esters is carried out by reacting a hydroxyl-substituted compound of formula (II) with an activated amino acyl, phosphoryl or hemisuccinyl derivative. The resulting product is then deprotected to provide the desired prodrug ester. Other prodrugs include a hydroxyl-substituted compound of formula II wherein the hydroxyl group is functionalized with a substituent of the formula $—CH(R_{20})OC(O)R_{21}$ or $—CH(R_{20})OC(S)R_{21}$ wherein $R_{21}$ is loweralkyl, haloalkyl, alkoxy, thioalkoxy or haloalkoxy and $R_{20}$ is hydrogen, loweralkyl, haloalkyl, alkoxycarbonyl, aminocarbonyl, alkylaminocarbonyl or dialkylaminocarbonyl. These prodrugs can be prepared by condensation of the hydroxyl group with an activated aldehyde followed by acylation of the intermediate hemiacetal.

In general, the tablet formulation of this invention is prepared by mixing the compound of formula II with the filler and one half of the total amount of the polycarboxylic acid. This mixture is granulated with water or ethanol or an ethanol/water mixture. The granules are dried and screened to the desired size. The granules are then mixed with the remainder of the polycarboxylic acid and any binders, lubricants and/or disintegrants or other additives. After blending, this mixture is compressed into tablets.

The following examples will serve to further illustrate the invention.

EXAMPLE 1A

Tablet Composition No. 1

| Component | Amount per Tablet mg | % |
| --- | --- | --- |
| Compound I · HCl | 107.2 | 30.6 |
| Citric acid | 50.0 | 14.3 |
| Avicel ® | 150.0 | 42.8 |
| Crospovidone | 40.0 | 11.4 |
| Magnesium stearate | 3.0 | 0.9 |
| | 350.2 | 100.0 |

Compound I (HCl salt, 5.4 grams) was mixed with the Avicel® (7.5 grams) and citric acid (1.25 grams) was added. This mixture was granulated with 200 proof ethanol. The ethanol was added with continuous mixing either by dropwise addition or by spraying into the powders. The granulated material was dried in an oven overnight at 50° C. to 60° C. The granules were screened through a 20 mesh screen.

The crospovidone (2.0 grams) and magnesium stearate (0.15 grams) were added to the granules and the remainder of the citric acid (1.25 grams) was added. After blending, this mixture was compressed into tablets.

EXAMPLE 1B

Tablet Composition No. 2

| Component | Amount per Tablet mg | % |
| --- | --- | --- |
| Compound I · HCl | 107.2 | 30.3 |
| Citric acid | 50.0 | 14.1 |
| Avicel ® | 150.0 | 42.4 |
| Brij ® 35 | 2.4 | 0.7 |
| Tween ® 80 | 0.8 | 0.2 |
| Crospovidone | 40.0 | 11.3 |
| Magnesium stearate | 3.0 | 0.8 |
| | 353.4 | 100.0 |

Compound I (HCl salt, 5.4 grams) was mixed with Avicel® (7.5 grams) and citric acid (1.25 grams) and screened through a 20 mesh screen. A solution of Brij®35 (0.12 grams) and Tween® 80 (0.04 grams) in about 1.0 ml of 200 proof ethanol was added dropwise to the granulate. Alcohol (200 proof ethanol) was added dropwise to complete the granulation. The granules were dried overnight in an oven at 60° C. and subsequently screened through a 20 mesh screen.

Crospovidone (2.0 grams) and magnesium stearate (0.15 grams) were added to the granules and the remainder of the citric acid (1.25 grams) was added. After blending, this mixture was compressed into tablets.

EXAMPLE 1C

Tablet Composition No. 3

| Component | Amount per Tablet | |
|---|---|---|
| | mg | % |
| Compound I · mesylate | 120.5 | 20.1 |
| Malonic acid | 50.0 | 8.3 |
| Avicel ® | 300.0 | 50.0 |
| Brij ® 35 | 18.0 | 3.0 |
| Tween ® 80 | 6.0 | 1.0 |
| Emulphor ® 719 | 6.0 | 1.0 |
| Crospovidone | 50.0 | 8.3 |
| Sodium starch glycolate | 50.0 | 8.3 |
| | 600.5 | 100.0 |

Compound I (mesylate salt, 1.45 grams) was mixed with Avicel® (2.4 grams) and granulated with 1.8 ml of a solution of Brij® 35 (1.2 grams), Tween® 80 (0.4 grams) and Emulphor® 719 (0.4 grams) in 10 ml of 200 proof ethanol. The granulation was dried at 50° C. in a vacuum oven for at least 2 hours and then screened through a 20 mesh screen. Avicel® (1.2 grams), malonic acid (0.6 grams), sodium starch glycolate (0.6 grams) and crospovidone (0.6 grams) were added to the granules and blended. After blending, this mixture was compressed into tablets.

EXAMPLE 1D

Tablet Composition No. 4

| Component | Amount per Tablet | |
|---|---|---|
| | mg | % |
| Compound I · mesylate | 120.5 | 20.2 |
| Citric acid | 75.0 | 12.6 |
| Avicel ® | 300.0 | 50.4 |
| Crospovidone | 50.0 | 8.4 |
| Sodium starch glycolate | 50.0 | 8.4 |
| | 595.5 | 100.0 |

Compound I (mesylate salt, 1.45 grams) was mixed with Avicel® (3.6 grams) and citric acid (anhydrous, 0.9 grams) and dry blended until a homogeneous mixture was obtained. Sodium starch glycolate (0.6 grams) and crospovidone (0.6 grams) were added and blended. After blending, this mixture was compressed into tablets.

EXAMPLE 2A

Preparation Of A Tablet Composition Comprising Compound III

Using the process of Example 1, tablet compositions of compound III can be prepared.

EXAMPLE 2B

Preparation Of A Tablet Composition Comprising the Compound of Example 9

Using the process of Example 1, tablet compositions of the compound of Example 9 can be prepared.

EXAMPLE 3

(2S)-2-Benzyl-3-(1-methyl-piperazin-4-ylsulfonyl)propionyl-(L)-(4-Thiazolyl)Ala Amide of (2S, 3R, 4S)-2-Amino-1-cyclohexyl-3,4-dihydroxy-6-methylheptane

EXAMPLE 3A

Methyl 3-Hydroxy-2-methylene-3-phenylpropionate

A mixture of benzaldehyde (82.1 mL, 0.81 mol), methyl acrylate (109.1 mL, 1.211 mol), 1,4-diazabicyclo (2,2,2) octane (13.6 g, 0.12 mol), and acetic acid (1.4 mL, 0.024 mol) was allowed to stir at 35° C. for 60 h, at which point the reaction was determined to have proceeded to 70% completion by $^1$H NMR. Methyl acrylate (20.9 mL, 0.23 mol) was then added and the solution was allowed to react at 35° C. for an additional 48 h. The mixture was diluted with diethyl ether (1.0 L) and was washed with 2×200 mL portions of a pH 7 phosphate buffer. After concentration in vacuo, the remaining mixture was distilled at reduced pressure (12 mm) to afford 6.5 g of unreacted benzaldehyde and 130.0 g (90%) of the desired product as a colorless oil: b.p. 130° C. (12 mm); IR (film) 1718, 1440 cm$^{-1}$; $^1$H NMR (CDCl$_3$) δ3.67 (s, 3H), 5.52 (br s, 1H), 5.83–5.85 (m, 1H), 6.29–6.31 (m, 1H), 7.23–7.39 (m, 5H); $^{13}$C NMR (75 MHz, CDCl$_3$) δ51.8, 72.9, 125.8, 126.5, 127.7, 128.3, 141.2, 141.9, 166.6.

EXAMPLE 3B (Z)-1-Bromo-2-carbomethoxy-3-phenyl-2-propene

To a 2 L, 3-neck Morton flask fitted with a thermometer, a mechanical stirrer, and an addition funnel was added the resultant compound from Example 3A (305.9 g, 1.585 mol) followed by addition of 48% HBr (505 mL, 4.46 mol) in one portion. The flask was immersed in an ice-water bath, at which time concentrated sulfuric acid (460 mL, 8.62 mol) was added dropwise over 90 min and the internal temperature of the reaction mixture was maintained at 23°–27° C. throughout the addition process. After removal of the ice-water bath, the mixture was allowed to stir at ambient temperature overnight. The solution was then transferred to a separatory funnel and the organic layer was allowed to separate from the acid layer. The acids were drained and the organic layer was diluted with 2 L of a 1:1 ethyl acetate/hexane solution, washed with saturated aqueous sodium bicarbonate solution (1 L), dried over sodium sulfate, and concentrated to yield 400 g (99%) of the desired product as a light yellow oil, which was used without any additional purification: b.p. 180° C. (12 mm); IR (film) 1718, 712 cm$^{-1}$; $^1$H NMR (CDCl$_3$) δ3.89 (s, 3H), 4.40 (s, 2H), 7.38–7.45 (m, 3H), 7.56–7.60 (m, 2H), 7.83 (s, 1H); $^{13}$C NMR (75 MHz, CDCl$_3$) δ 26.77, 52.47, 128.63, 128.87, 129.61, 134.20, 142.95, 166.62.

EXAMPLE 3C (Z)-2-Carbomethoxy-3-phenyl-2-propene-1-sulfonic Acid Sodium Salt To a 12 L, 3-neck round bottom flask fitted with a mechanical stirrer, thermometer and an addition funnel was added the resultant product from Example 3B (400 g, 1.57 mol) and methanol (4 L). The mixture was warmed to 50° C. and a solution of sodium sulfite (199 g, 1.57 mol) dissolved in water (4 L) was added over 75 min while the internal temperature of the flask was maintained at 50° C. After the addition was complete, the clear solution was allowed to stir at 50° C. for an additional 45 min. The reaction mixture in solution was taken to the next step without additional purification. The compound may be isolated by concentration to an amorphous powder, which is contaminated with an equivalent of sodium bromide: IR (KBr) 1711, 1628, 1215 cm$^{-1}$; $^1$H NMR (DMSO D-6) δ3.70 (s, 3H), 3.77 (s, 2H), 7.33–7.41 (m, 3H), 7.48 (s, 1H), 7.87–7.89 (m, 2H); $^{13}$C NMR (75 MHz, DMSO D-6) δ49.88, 51.93, 127.36, 128.33, 128.91, 129.82, 134.75, 139.06, 168.60.

EXAMPLE 3D

2-Carbomethoxy-3-phenylpropane-1-sulfonic Acid Sodium Salt

To the 8 L of 1:1 methanol/water mixture containing the resultant compound from Example 3C was added 60 g of W-24 raney nickel. The resulting suspension was pressurized under 50 psi of hydrogen and was allowed to shake on a Parr shaker for 24 h, at which time an additional 20 g of raney nickel catalyst was added. After 6 h under 50 psi of hydrogen, the catalyst was removed by filtration and the solution was concentrated to dryness. To the dry white solid was added ethyl acetate (6 L) and heptane (4 L) and the solution was vigorously stirred with a mechanical stirrer overnight. The white suspension was removed by filtration yielding 530 g (88%) of the desired product as an amorphous powder that was contaminated with approximately one equivalent of NaBr. The compound was used without any additional purification: IR (KBr) 1740, 1215, 1050 cm$^{-1}$. $^1$H NMR (DMSO D-6) δ2.48–2.54 (m, 1H), 2.74–2.87 (m, 2H), 2.91–3.04 (m, 2H), 3.48 (s, 3H), 7.12–7.32 (m, 5H); $^{13}$C NMR (75 MHz, D$_2$O/DMSO D-6) δ38.18, 44.80, 52.67, 52.82, 127.42, 129.13, 129.34, 138.14, 176.84.

EXAMPLE 3E

2-Carbomethoxy-3-phenyl-1-propanesulfonyl Chloride

To a 3 L round bottom flask was added the resultant compound from Example 3D (530 g, 1.39 mol) and toluene (520 mL) followed by the addition of PCl$_5$ (317 g, 1.52 mol). The mixture was warmed to 50° C. with stirring for 45 min. It was then diluted with toluene (1 L) and was filtered through celite. After concentration in vacuo, 371 g (96%) of the desired product was obtained as a light brown oil: IR (film) 1740, 1380, 1170 cm$^{-1}$; $^1$H NMR (CDCl$_3$); δ2.92 (dd, 1H, J= 8.1, 14.0), 3.17 (dd, 1H, J=6.6, 14.0), 3.41–3.50 (m, 1H), 3.67 (dd, 1H, J= 3.3, 14.3), 3.72 (s, 3H), 4.20 (dd, 1H, J= 8.8, 14.3), 7.15–7.18 (m, 2H), 7.25–7.35 (m, 3H); $^{13}$C NMR (75 MHz, CDCl$_3$) δ 37.26, 42.88, 52.65, 64.89, 127.49, 128.87, 128.92, 35.61, 171.79.

EXAMPLE 3F

Methyl 2-Benzyl-3-(1-methyl-piperazin-4-ylsulfonyl)propionate

To a 1 L round bottom flask was added the resultant compound from Example 3E (84.5 g, 0.305 mol) and dichloromethane (305 mL). The mixture was cooled to 0° C. in an ice water bath and a solution of N-methyl piperazine (35.5 mL, 32.1 g) dissolved in dichloromethane (305 mL) was added dropwise with vigorous stirring over 90 min. After the addition was completed, the ice-water bath was removed and the mixture was stirred an additional 4 h while warming to ambient temperature. The solution was then poured into a separatory funnel containing 1 L of a 5% aqueous NaOH solution. The layers were partitioned and the organic layer was dried over potassium carbonate. Concentration in vacuo yielded an oil, which was filtered through 200 g of silica gel using 4:1 hexane/ethyl acetate as an eluant. Concentration gave 84.3 g (81%) of the desired product as a yellow oil: IR (film); 1735, 1165, 955 cm$^{-1}$; $^1$H NMR (CDCl$_3$) δ 2.30 (s, 3H), 2.42 (t, 4H, J=4.8), 2.88 (dd, 1H, J= 7.7, 14.0), 2.93 (dd, 1H, J=3.7, 14.0), 3.06 (dd, 1H, J= 7.0, 13.6), 3.18–3.27 (m, 5H), 3.43 (dd, 1H, J= 8.82, 13.9), 3.67 (s, 3H), 7.14–7.17 (m, 2H), 7.24–7.34 (m, 3H); $^{13}$C NMR (75 MHz, CDCl$_3$) δ37.91, 42.22, 45.36, 45.83, 49.61, 52.21, 54.36, 127.06, 128.66, 128.92, 129.06, 136.79, 173.33.

EXAMPLE 3G (2S) 2-Benzyl-3-(1-methyl-piperazin-4-ylsulfonyl)propionic Acid

The resultant racemic ester from Example 3F (135 g, 397 mmol) was suspended in acetone (300 mL) and water (900 mL). While being stirred vigorously at a temperature of 35° C., a crude preparation of Subtilisin Carlsberg (10 mL, Alcalase 2.4 L, Novo Laboratories) was added. Sodium hydroxide solution (6M) was used to maintain the reaction at pH 7.5–8.0. After 3 days, the acetone was removed under reduced pressure and the aqueous phase was extracted with CHCl$_3$ (1 L) to remove the unreacted ester. The aqueous phase was adjusted to pH 7 with 3M HCl and was desalted by eluting through a column of Amberlite XAD-16(2 kg, prewashed sequentially with water, methanol, and water) using a water to water/methanol gradient. Evaporation of the solvent afforded 46 g (70%) of a white solid: mp 184.5° C.; TLC (25% ethyl acetate/25% water/25% acetic acid/25% n-butanol) R$_f$=0.43;

Anal. (C$_{15}$H$_{22}$N$_2$O$_4$S·0.25 H$_2$O) Calcd: C, 54.44; H, 6.85; N, 8.47. Found: C, 54.77; H, 6.53; N, 8.39.

EXAMPLE 3H

Diethyl (2-Bromoallyl)acetamidomalonate

To a stirred mixture of diethyl acetamidomalonate (217 g, 1.0 mol) and 2,3-dibromopropene (240 g, 1.2 mol) in dry tetrahydrofuran (2.50 L), under nitrogen, was added sodium hydride (26.4 g, 1.1 mol) in several portions. The reaction mixture was stirred at room temperature for 30 min, then heated to reflux. After heating for 18 h, the resultant slurry was cooled to room temperature and suction filtered through a short pad of silica gel. The solid residue was washed with tetrahydrofuran (2×50 mL), and the filtrates were combined and concentrated. The residue was dissolved in ethyl acetate (2.0 L), washed with water and brine, and then was dried over MgSO$_4$. Filtration and concentration gave a yellow oil which solidified upon drying. The resultant solid was recrystallized from a mixture of hot ethyl acetate/hexane to give 301 g (89%) of the desired product: m.p. 85°–87° C. $^1$H NMR (300 MHz, CDCl$_3$) δ1.28 (t, J= 7.4 Hz, 6H), 2.04 (s, 3H), 3.57 (s, 2H), 4.27 (m, 4H), 5.55 (bs, 1H), 5.61 (bs, 1H), 6.82 (broad, 1H); IR (KBr) 1745, 1635 cm$^{-1}$. Anal. Calcd. for C$_{12}$H$_{18}$BrNO$_5$: C, 42.87; H, 5.40; Br, 23.77; N, 4.12. Found: C, 43.25; H, 5.56; Br, 22.97; N, 4.12.

EXAMPLE 3I

Diethyl (3-Bromo-2-oxo-propyl)acetamidomalonate

To a cold (0° C.), stirred solution of the resultant compound from Example 3H (280 g, 0.83 mol) in a mixture of 2:1 acetonitrile/water (1.68 L) was added solid N-bromosuccinimide (193 g, 1.08 mol) in three portions over a period of 15 min. The resultant orange mixture was stirred at 0° C. for an additional period of 1 h and then was allowed to warm to room temperature. After 4 h, the reaction mixture was treated with 10% aqueous sodium thiosulfate, diluted with ethyl acetate, and washed sequentially with water, 10% aqueous NaHSO$_4$ (3×), water, and brine. Drying (MgSO$_4$) and concentration afforded a yellow solid which was recrystallized from a mixture of ethyl acetate and hexane to give 247 g (85%) of the desired compound as a white solid: m.p. 97°–98.5° C. $^1$H NMR (300 MHz, CDCl$_3$) δ1.25 (t, J= 7.5 Hz, 6H), 2.01 (s, 3H), 3.87 (s, 2H), 3.93 (s, 2H), 4.25 (q, J= 7.5 Hz, 4H), 7.0 (broad, 1H); IR (KBr) 1760, 1732, 1634 and 1209 cm$^{-1}$. Anal. Calcd. for C$_{12}$H$_{18}$BrNO$_6$: C, 40.93; H, 5.15; Br, 22.62; N, 3.98. Found: C, 41.05; H, 5.23; Br, 23.28; N, 3.93.

EXAMPLE 3J

Diethyl (4-Thiazolylmethyl)acetamidomalonate

A 5 L, 3-neck round bottom flask equipped with a mechanical stirrer, stopper and a drying tube was charged with the resultant compound from Example 3I (325 g, 0.92 mol) and flushed with nitrogen. A freshly prepared solution of thioformamide in tetrahydrofuran (0.8M, 1.25 L) was added in one portion. The reaction mixture was stirred at room temperature for 4 h. The resultant slurry was then diluted with ether (1.25 L) and cooled to 0° C. The solid was then collected by suction filtration and washed with cold ether (3×) to give the title compound as the hydrobromide salt. This material was transferred to a 4 L separatory funnel, slurried with ethyl acetate (2 L) and basified by the careful addition of 2M aqueous NaOH. The organic layer was separated, washed with water and brine, and then dried over MgSO$_4$. Filtration and concentration afforded a pale yellow oil which solidified upon drying to give 242 g of the desired compound. This material was recrystallized from an ethyl acetate/hexane mixture to afford 185.6 g (64%) of pure material: m.p. 104°– 106° C. Anal. Calcd. for C$_{13}$H$_{18}$N$_2$O$_5$S: C, 49.67; H, 5.77; N, 8.91; S, 10.20. Found: C, 49.90; H, 5.72; N, 8.97; S, 10.29.

EXAMPLE 3K

N-Acetyl-3-(4-thiazolyl)-DL-alanine Ethyl Ester

To a stirred solution of the resultant compound from Example 3J (185.6 g, 0.59 mol) in a mixture of tetrahydrofuran (620 mL) and ethanol (310 mL) was added aqueous 2M LiOH (325 mL, 0.65 mol) dropwise over 20 min. After stirring at room temperature for 2.5 h, the reaction mixture was concentrated and the resultant aqueous mixture was extracted with ether (3×200 mL), adjusted to pH 3 with 3M HCl, and concentrated under reduced pressure. Residual water was removed by evaporating portions of toluene (2×200 mL). The residue was diluted with toluene (1.5 L) and the resultant slurry was heated to reflux with separation of residual water (Dean-Stark trap). After 3 h the reaction mixture was cooled to room temperature, diluted with ethyl acetate (1.5 L) and suction filtered through SiO$_2$ (60 g). The solids were washed with additional ethyl acetate (4×500 mL) and the combined organics were concentrated to afford a pale yellow oil which solidified on drying (0.5 torr) to afford 119.6 g (84%) of the desired compound: m.p. 58°–62° C.

EXAMPLE 3L

N-Acetyl-3-(4-thiazolyl)-L-alanine and N-Acetyl-3-(4-thiazolyl)-D-alanine Ethyl Ester A 5 L, 3-neck round bottom flask equipped with a mechanical stirrer was charged with the resultant compound from Example 3K (210 g, 0.87 mol), distilled water (1.6 L), and 1M aqueous KCl (0.8 L). The homogeneous solution was adjusted to pH 7.0 with 0.1M NaOH and then was treated with Subtilisin Carlsberg (1.8 g) dissolved in 0.1 M aqueous KCl (25 mL). The reaction mixture was stirred at room temperature with 1.0M NaOH added as required to maintain the pH at 6.25–7.25. After 4 h, 430 mL of base had been consumed and the reaction was judged to be complete. The reaction mixture was then extracted with chloroform (4×1.5 L), the aqueous phase was carefully acidified to pH 4 with 2M HCL and then was concentrated under reduced pressure. Residual water was removed by consecutive evaporation from toluene (3×500 mL) and ethanol (3×500 mL). The residue was taken up in warm ethanol and suction filtered to remove inorganic salts. The solids were washed with warm ethanol (3×400 mL) and the filtrates were concentrated to afford 92.6 g (50%) of N-acetyl-3-(4-thiazolyl)-L-alanine as a white solid: m.p. 186° C.

The combined chloroform fractions from the extractions were washed with saturated aqueous NaHCO$_3$, water, and brine and then were dried over MgSO$_4$. Filtration and concentration gave 103 g (49%) of N-acetyl- 3-(4-thiazolyl)-D-alanine ethyl ester. This material could be further purified by recrystallization from ethyl acetate/hexane: m.p. 79°–80.5° C.

EXAMPLE 3M

Epimerization of N-Acetyl-3-(4-thiazolyl)-D-alanine Ethyl

A 2 L round bottom flask equipped with a magnetic stirrer, reflux condenser, and nitrogen inlet was charged with sodium (0.96 g, 0.045 mol) and ethanol (900 mL) and the mixture was allowed to reflux until the sodium was consumed. The resultant solution of sodium ethoxide was cooled slightly, and N-acetyl-3-(4-thiazolyl)-D-alanine ethyl ester from Example 3L (102 g, 0.42 mol) was added. The reaction mixture was then heated to reflux. After 3 h the solution was cooled to room temperature, quenched with glacial acetic acid (0.045 mol) and concentrated to remove ethanol. The residue was diluted with ethyl acetate, washed with water and brine and dried over $MgSO_4$. Filtration and concentration gave a yellow oil which was purified by recrystallizing from a mixture of hot ethyl acetate and hexane to yield 89 g (87%) of material identical to that obtained from Example 3K.

EXAMPLE 3N

3-(4-Thiazolyl)-L-alanine Dihydrochloride

A 2 L round bottom flask equipped with a magnetic stirrer was charged with N-acetyl-3-(4-thialzoyl)-L-alanine from Example 3L (92.6 g, 0.43 mol) and 6M HCl (1 L). The resultant solution was heated to reflux. After 3 h the mixture was allowed to cool to room temperature. The solution was then concentrated under reduced pressure, evaporated from toluene (3×200 mL), and dried under vacuum overnight to give 120 g of a slightly wet solid. This material was used in the next reaction without further purification.

EXAMPLE 3O

N-Boc-3-(4-thiazolyl)-L-alanine

A 4 L Erlenmeyer flask equipped with a mechanical stirrer was charged with the resultant compound from Example 3N (125.9 g) and tetrahydrofuran (1.5 L) and the mixture was adjusted to pH 6.6 with saturated aqueous sodium bicarbonate. The resultant solution was then adjusted to pH 8.9 with 3.0M NaOH and a solution of di-tert-butyldicarbonate (117.8 g, 0.51 mol) in tetrahydrofuran (150 mL) was added. The reaction mixture was vigorously stirred at room temperature for 40 h. The tetrahydrofuran was removed under vacuum, the pH of the residue was adjusted to 2.0 with 3.0M HCl and the mixture was extracted with ethyl acetate (3×300 mL). The combined extracts were dried over $MgSO_4$, filtered, and concentrated to give 150 g of a white solid. Recrystallization from hot 1:1 ethyl acetate/hexane (1.06 L) gave 107.6 g (82 % from the resultant compound of Example 3L) of the desired compound: m.p. 115° C.; $[\alpha]_D$=+129.8 (c= 1.04, $CHCl_3$).

Anal. Calcd. for $C_{11}H_{16}N_2O_2$: C, 48.53; H, 5.88; N, 10.29. Found: C, 48.58; H, 5.91; N, 10.17.

EXAMPLE 3P

Boc-L-(4-Thiazolyl)Ala Amide of (2S, 3R, 4S)-2-Amino-1-cyclohexyl-3,4-dihydroxy-6-methylheptane (2S, 3R, 4S)-2-[ (tert-Butyloxycarbonyl) amino]- 1-cyclohexyl-3,4-dihydroxy-6-methylheptane (5.05 g, 14.7 mmol, Luly et al., *J. Org. Chem.* 1988, 53, 6109) was stirred for 90 min in 4M HCl in ethanol and then evaporated. Ether was added and evaporated 3 times and the residue was dried under high vacuum. To this residue was added 1-hydroxybenzotriazole (5.57 g, 41.2 mmol), the resultant acid from Example 3O (4.00 g, 14.7 mmol), dimethylformamide (60 mL) and N-methylmorpholine (3.40 mL, 30.9 mmol). The mixture was cooled to −23° C. treated with 1-(3-dimethylaminopropyl)-3-ethylcarbodiimide hydrochloride (4.03 g, 21.0 mmol). After 2 h at −23° C. and 21 h at ambient temperature the mixture was poured into saturated $NaHCO_3$ solution and extracted into ethyl acetate. The organic layer was washed with water and brine, then dried over $Na_2SO_4$ and evaporated to a white solid which was recrystallized from 1:15 (v/v) methylene chloride/ether (multiple crops) affording 6.28 g (86%) of the desired product as a flaky white solid: m.p. 159°–160° C.; TLC (15% $CH_3OH$/85% $CHCl_3$) $R_f$=0.63; $^1$H NMR ($CDCl_3$) δ8.78 (1H, d), 7.14 (1H, d), 6.18 (2H, br d), 4.44 (1H, dd), 4.27 (1H, m), 4.10 (1H, m), 3.37 (1H, dd), 3.30–3.12 (3H, m), 1.89 (1H, septet), 1.46 (9H, s), 0.94 (3H, d), 0.88 (3H, d).

Anal. Calcd. for $C_{25}H_{43}N_3O_5S$: C, 60.33; H, 8.71; N, 8.44. Found: C, 60.43; H, 8.68; N, 8.51.

EXAMPLE 3Q

H-L-(4-Thiazolyl)Ala Amide of (2S, 3R, 4S)-2-Amino-1-cyclohexyl-3,4-dihydroxy-6-methylheptane Trifluoroacetic acid (50 mL) was slowly added via cannula to a solution of the resultant compound from Example 3P (6.27 g, 12.6 mmol) in methylene chloride (50 mL) at 0° C. The reaction was stirred 3 h at 0° C. and concentrated in vacuo (40° C. bath) to an oil which was basified to pH 10–11 with aqueous $K_2CO_3$. The product was extracted into chloroform, dried over $Na_2SO_4$, filtered, and concentrated to a foam. Recrystallization from 1:4 (v/v) methylene chloride/hexane gave 5.00 g (100%) of the desired product as a fluffy white solid: m.p. 111°–112° C.; TLC (15% $CH_3OH$/85% $CHCl_3$) $R_f$= 0.46; $^1$H NMR ($CDCl_3$) δ8.77 (1H, d), 7.40 (1H, br d), 7.13 (1H, d), 4.54 (1H, m), 4.25 (1H, m), 3.80 (1H, dd), 3.33 (1H, dd), 3.25–3.12 (3H, m), 0.95 (3H, d), 0.86 (3H, d).

Anal. Calcd. for $C_{20}H_{35}N_3O_3S$: C, 60.42; H, 8.87; N, 10.57. Found: C, 60.05; H, 8.65; N, 10.42.

EXAMPLE 3R

(2S )-2-Benzyl-3-(1-methylpiperazin-4-ylsulfonyl) propionyl-(L)-( 4-Thiazolyl)Ala Amide of (2S, 3R, 4S)-2-Amino-1-cyclohexyl-3,4-dihydroxy-6-methylheptane To the resultant acid from Example 3G (1.000 g, 3.064 mmol), the resultant amine from Example 3Q (1.110 g, 2.792 mmol), and 1-hydroxybenzotriazole (1.022 g, 7.563 mmol) in dimethylformamide (20 mL) was added N-methylmorpholine (0.35 mL, 3.2 mmol). The mixture was cooled to −23° C. and treated with 1-(3-dimethylaminopropyl)-3-ethylcarbodiimide hydrochloride (0.760 g, 3.96 mmol). After 2 h at −23° C. and 14 h at ambient temperature, the reaction was poured into saturated $NaHCO_3$ solution (100 mL) and extracted into ethyl acetate (2×50 mL) which was washed with water (2×50 mL) and brine (50 mL) and then was dried over $Na_2SO_4$ and evaporated to afford 1.94 g. Recrystallization from ethanol (15 mL)/hexane (90 mL) afforded 1.559 (79%) of a white solid: m.p. 169°–170° C.; TLC (10% $CH_3OH$/90% $CHCl_3$) $R_f$= 0.40; $^1$H NMR ($CDCl_3$) δ8.73 (1H, d), 7.43 (1H, d), 7.37–7.16 (6H, m), 6.23 (1H, d), 4.63 (1H, dd), 2.30 (3H, s), 0.95 (3H, d), 0.87 (3H, d).

Anal. Calcd. for $C_{35}H_{55}N_5O_6S_2$·0.75 $H_2O$: C, 58.43; H, 7.91; N, 9.73. Found: C, 58.51; H, 7.74; N, 9.60.

EXAMPLE 4

Alternative Preparation of N-Boc-3-(4-thiazolyl)-L-alanine

EXAMPLE 4A

Ethyl (2-Bromoallyl)acetamidoacetate

To a solution of the product of Example 3H (3.36 g, 10.0 mmol) in dimethylformamide (10 mL) was added sodium chloride (586 mg, 10.0 mmol), water (360 μL, 20 mmol) and 4N hydrochloric acid in dioxane (0.12 mL, 0.5 mmol). The reaction vessel was placed under a positive nitrogen pressure. The reaction mixture was heated at reflux for 24 hours and then concentrated in vacuo. The residue obtained was diluted with water (5 mL) and extracted with ether (3×15 mL). The combined organic extracts were decolorized with charcoal (0.5 g), dried over magnesium sulfate, filtered, and concentrated in vacuo to afford the title product (2.51 g, 95%) as a pale yellow oil. $^1$H NMR (300 MHz, $CDCl_3$) δ1.29 (t, 3H), 2.04 (s, 3H), 2.99 (m, 2H), 4.22 (q, 2H), 4.79 (m, 1H), 5.53 (d, 1H), 5.68 (m, 1H), 6.44 (d, 1H); IR (film) 1195, 1220, 1370, 1540, 1660, 1740, 2990, 3050, and 3300 cm$^{-1}$. MS (DCI/$NH_3$) m/e 264/266 (M+H)$^+$, 281/283 (M+H+$NH_3$)$^+$.

Anal. Calcd. for $C_9H_{14}NO_3Br$: C, 40.92; H, 5.34; N, 5.30. Found: C, 42.04; N, 5.48; N, 5.26.

EXAMPLE 4B

N-Boc-(2-Bromoallyl)glycine

A slurry of the product of Example 4A (16.2 g, 61.3 mmol) in 0.1N potassium chloride solution (300 mL) containing 0.2M pH 7.0 phosphate buffer (30 mL) was treated with a solution of Subtilisin Carlsberg (4 mg) in 0.1N potassium chloride solution (3 mL). The pH was maintained between 6.50 and 7.25 by addition of 2.0N sodium hydroxide solution via a pH-Stat. After 25 minutes, the rate of hydrolysis noticeably slowed; and the unreacted D-ester was extracted with methylene chloride (3×150 mL). The resulting aqueous phase was treated with cobalt(II) acetate (6 mg) and Acylase I (80 mg). The reaction mixture was stirred for 4 hours and determined to be complete.

The pH of the reaction mixture was adjusted to 10 by the addition of solid sodium carbonate. The resulting solution was treated with di-tert-butyl dicarbonate (6.55 g, 30 mmol) dissolved in THF (100 mL) and vigorously stirred for 16 hours. The aqueous solution was washed with hexane (200 mL) to remove any unreacted protecting-reagent. The aqueous layer was adjusted to pH 2.5 by the addition of solid potassium hydrogen sulfate and extracted with ethyl acetate (2×200 mL). The combined organic layers were washed with brine (100 mL), dried over magnesium sulfate, and concentrated in vacuo to give the title compound (7.30 g, 81%) as a pale yellow crystalline solid. [$\alpha$]D at 25° C.=−9.86° (MeOH), c= 1.085. $^1$H NMR (300 MHz, $CDCl_3$) δ1.48 (s, 9H), 2.91 (m, 2H), 4.52 (m, 1H), 5.19 (d, 0.5H), 5.53 (m, 1H), 5.71 (s, 1H), 6.79 (d, 0.5H), 11.3 (s, 1H); IR ($CDCl_3$) 1150, 1250, 1400, 1500, 1620, 1640, 1710, 3000, 3350, and 3520 cm$^{-1}$. (DCI/$NH_3$) m/e 311/313 (M+H+$NH_3$)$^+$. Anal. Calcd. for $C_{10}H_{16}NO_4Br$: C, 42.12; H, 5.66; N, 4.91. Found: C, 41.38; H, 5.59; N, 4.75.

EXAMPLE 4C (2R)-N-Boc-2-Amino-5-bromo-4-oxopentanoic Acid

To a solution of the product of Example 4B (2.00 g, 6.80 mmol) in water (30 mL) and tetrahydrofuran (15 mL) cooled to 0° C. was added N-bromosuccinimide (1.45 g, 8.16 mmol) in three portions over twenty minutes. After the addition was complete, the ice bath was removed and the solution was stirred for four hours. The tetrahydrofuran was removed in vacuo and the product was extracted with ethyl acetate (3×35 mL). The organic extracts were combined and washed with 5% sodium chloride solution (25 mL) and brine (25 mL), dried over magnesium sulfate, and concentrated in vacuo to afford the title compound (1.70 g, 81%). $^1$H NMR (300 MHz, $CDCl_3$) δ1.45 (s, 9H), 3.30 (m, 2H), 3.93 (s, 2H), 4.61 (m, 1H), 5.51 (d, 1H). MS (DCI/$NH_3$) m/e 310/312 (M+H)$^+$, 327/329 (M+H+$NH_3$)$^+$.

EXAMPLE 4D (2R)-N-Boc-2-Amino-3-(4-thiazolyl)propanoic Acid

To a solution of the product of Example 4C (91 mg, 0.293 mmol) in tetrahydrofuran (5 mL) was added thioformamide (17.7 mg, 0.29 mmol). [Thioformamide was prepared by reacting a slight excess of phosphorus pentasulfide with formamide in tetrahydrofuran. The resulting solution was diluted with hexanes and filtered through a silica gel plug and stored at −25° C.] The resulting solution was allowed to stand for sixteen hours and then concentrated in vacuo to afford a residue which was partitioned between diethyl ether and aqueous sodium bicarbonate. The aqueous layer was washed with ether (2×10 mL) and methylene chloride (10 mL), adjusted to pH 2.3 with solid potassium hydrogen sulfate, and extracted with ether (3×20 mL). The combined organic extracts were dried over magnesium sulfate and concentrated in vacuo to afford the title compound as a white crystalline solid (55 mg, 71%). $^1$H NMR (300 MHz, $CDCl_3$) δ 1.48 (s, 9H), 3.48 (m, 2H), 4.52 (m, 1H), 5.61 (m, 1H), 7.18 (d, 1H), 8.91 (d, 1H).

EXAMPLE 5

Alternative Preparation of (2R)-N-Boc-2-Amino-5-bromo-4-oxopentanoic acid

EXAMPLE 5A

Diethyl (2-Chloroallyl)acetamidomalonate

To a suspension of 95% sodium hydride (17.2 g, 680 mmol) in tetrahydrofuran (1.2 L) was added 2,3-dichloropropene (100 g, 900 mmol), diethylacetamidomalonate (146 g, 672 mmol) and tetrabutylammonium bromide (6.00 g). The resulting thick suspension was warmed at reflux under nitrogen for 20 hours. The reaction mixture was concentrated in vacuo and the resulting residue was partitioned between water (200 mL) and a mixture of ether (300 mL) and methylene chloride (100 mL). The organic phase was washed with 5% sodium chloride solution (200 mL) and brine (200 mL), dried over magnesium sulfate, filtered, and concentrated in vacuo. The resulting solid (195 g) was dissolved in hot hexanes (1300 mL) and allowed to cool to room temperature and sit overnight to afford the title compound as a crystalline solid (157 g, 80%). mp 76.3° C. $^1$H NMR (300 MHz, CDCl$_3$) δ1.29 (t, 6H), 2.05 (s, 3H), 3.48 (s, 2H), 4.28 (m, 4H), 5.18 (m, 1H), 5.29 (m, 1H), 6.92 (bs, 1H); IR (CDCl$_3$) 1140, 1180, 1200, 1240, 1270, 1300, 1500, 1630, 1680, 1740, 2950, 2990, and 3300 cm$^{-1}$. MS (DCI/NH$_3$) m/e 292/294 (M+H)$^+$, 309/311 (M+H+NH$_3$)$^+$. Anal Calcd. for C$_{12}$H$_{18}$NO$_5$Cl: C, 49.41; H, 6.22; N, 4.80. Found: C, 49.18; H, 6.29; N, 4.75.

EXAMPLE 5B

Ethyl (2-Chloroallyl)acetamidoacetate

The product of Example 5A (137 g, 500 mmol) was hydrolyzed and decarboxylated by the procedure described in Example 2A to afford the title compound (105.4 g, 96%) as a pale yellow oil which crystallized upon standing. $^1$H NMR (300 MHz, CDCl$_3$) δ1.31 (t, 3H), 2.05 (s, 3H), 2.79 (m, 2H), 4.22 (q, 2H), 4.79 (m, 1H), 5.23 (m, 1H), 5.29 (m, 1H), 6.61 (m, 1H); IR 1200, 1220, 1280, 1300, 1370, 1440, 1550, 1638, 1659, 1740, 2890, 2990, 3050, and 3300 cm$^{-1}$. MS (DCI/NH$_3$) m/e 220/222 (M+H)$^+$, 237/239 (M+H+NH$_3$)$^+$. Anal. Calcd. for C$_9$H$_{14}$NO$_3$Cl: C, 49.21; H, 6.42; N, 6.38. Found: C, 46.58; H, 6.05; N, 6.02.

EXAMPLE 5C

(2R)-N-Boc-2-Amino-5-bromo-4-oxopentanoic acid

The product of Example 5B is treated according to the procedure of Example 4B and 4C to provide the desired product.

EXAMPLE 6

Alternative Preparation of 2(S) Benzyl-3-(1-methylpiperazin-4-ylsulfonyl)propionic acid

EXAMPLE 6A

2-Carbomethoxy-3-phenylpropane-1-sulfonic acid Sodium salt

To a 0.3M ethanolic solution of the product of Example 3B, (Z)-1-bromo-2-carbomethoxy-3-phenyl-2-propene, (0.98 molar equivalents) was added over one hour at 50° C. a 1.4M aqueous solution of sodium sulfite (1.0 molar equivalent). The mixture was stirred for 10 hours at 50° C. and then the ethanol was removed under reduced pressure at 50° C. Ethyl acetate (3 kg per 1 kg of bromide) was added and the mixture stirred for an additional 15 minutes and let stand for 10 minutes. The layers were separated and the aqueous layer was washed as above with two additional aliquots of ethyl acetate (1 kg per 1 kg of bromide).

Raney nickel (1 kg per 10 kg of aqueous solution) was added to the aqueous solution which was then evacuated and purged with nitrogen followed by hydrogen (3×) and placed under 40 psi of hydrogen for 6.5 to 9.5 hours. The Raney nickel was removed by filtration using nitrogen pressure, and the filtrate was concentrated under reduced pressure at 55° C. A 10% aqueous acetone solution (0.3 kg per 1 kg of starting bromide) was added to the residue obtained, and the mixture was warmed at 50° C. for 30 minutes. Additional acetone (3 kg per 1 kg of starting bromide) was slowly added over one hour to effect crystallization of the product. After stirring for one hour, the product was removed by filtration and washed with acetone to afford the title compound in 60–65%. m.p. 255° C. dec. A second crop was obtained by adding additional acetone (2.5 kg per 1 kg of starting bromide) and cooling to −20° C. for 10–12 hours and removing the second crop by filtration. An additonal 13–40% yield of title compound was obtained in that way.

EXAMPLE 6B

Methyl 2-Benzyl-3-(1-methylpiperazin-4-ylsulfonyl)propionate

The product of Example 6A (1 molar equivalent) was mixed with phosphorus pentachloride (1.5 molar equivalents) and warmed at 70°–75° C. for 3–4 hours. The reaction mixture was cooled to room temperature and then diluted with toluene (16.7 molar equivalents) and added to 10% aqueous sodium chloride solution (4 kg per 1 kg of phosphorus pentachloride) while maintaining the temperature below 40° C. The mixture was stirred for 5 minutes, allowed to settle for 15 minutes, and then the phases were separated. The sodium chloride wash was repeated as described above. The toluene phase was cooled to 5° C. and N-methylpiperazine (3 molar equivalents in 3 molar equivalents of toluene) was added maintaining the temperature below 15° C. The mixture was stirred for 4–6 hours and then washed with 8% aqueous sodium hydroxide (2×3.4 kg per 1 kg of phosphorus pentachloride). The combined basic washes were re-extracted with toluene (0.25 kg per 1 kg of sodium hydroxide solution). The combined toluene extracts were washed with water (1 kg per 1 kg of phosphorus pentachloride), and the toluene was removed by distillation at reduced pressure to afford the title compound (65–70%) as a viscous oil which crystallizes on standing. MS (DCI/NH$_3$) m/e 341 (M+H)$^+$.

EXAMPLE 6C

(2S)-2-Benzyl-3-(1-methylpiperazin-4-ylsulfonyl)propionic Acid

The product of Example 6B (69 kg, 20 mol) in acetone (420 kg)/water (960 kg) was adjusted to pH 8.0 using 1N sodium hydroxide. Alcalase™ (Novo Industries, Denamrk) (Subtilisin Carlsberg) (6.9 liters) was added and the pH was maintained between 7.9 and 8.4 by the addition of 1N sodium hydroxide. When 80% of the theoretical amount of sodium hydroxide had been consumed, the reaction was quenched by the addition of ethyl acetate. The reaction mixture was concentrated to half the original volume under reduced pressure and then washed with ethyl acetate (2×700 kg). The volume of the aqueous phase was concentrated by half and the pH adjusted to 5.2. The reaction mixture was treated with XAD-16 resin (50 kg), stirred for 18 hours, and applied to an XAD-16 resin column (50 kg). The column was eluted with water (500 kg) and then 35% ethanol in water (1000 kg) to afford a residue which was treated with isopropanol (270 kg) and warmed to 75° C. Upon cooling to room temperature and subsequently to −5° C. crystalline material was obtained. The solid was removed by filtration, washed with cold isopropanol (30 kg) and dried at 50° C. to afford the title compound (13 kg, 49%). MS (DCI/NH$_3$) m/e 327 (M+H)$^+$. This compound can be recrystallized from 1:1 isopropanol/water.

EXAMPLE 7

Alternative Preparation of 2(S)-2-Benzyl-3-(1-methylpiperazin-4-ylsulfonyl) propionyl-L-( 4-thiazolyl)Ala Amide of (2S, 3R, 4S)-2-Amino-1-cyclohexyl-3,4-dihydroxy-6-methylheptane

EXAMPLE 7A

(2S, 3R, 4S)-2-Amino-1-cyclohexyl-3,4-dihydroxy-6-methylheptane

A 3.5% solution of 2S-t-butyloxycarbonylamino- 1-cyclohexyl-3R, 4S-dihydroxy-6-methylheptane in 4N ethanolic hydrochloric acid was prepared at 0°–5° C. After 4 hours at 0°–5° C., nitrogen was bubbled through the reaction mixture to remove dissolved hydrochloric acid. The solvent was removed under reduced pressure at 50° C. to afford a solid which was dissolved in ethyl acetate and water. Potassium carbonate was added to bring the pH of the mixture to between 10 and 11, and the layers were separated. The aqueous layer was extracted with additional portions of ethyl acetate. The combined organic extracts were washed with water and brine, dried over magnesium sulfate, and concentrated under reduced pressure at 50° C. to afford a solid. The solid was crystallized by dissolving in a minimum amount of ethanol at 40° C. and then water was slowly added until the ratio of ethanol to water was 40/60 (w/w). The solution was cooled to 0°–5° C. for 2 hours and the product was collected by filtration. The solid was then dried under vacuum at 45° C. to provide title compound as a white crystalline solid (65–72%). m.p. 106°–108° C. MS (DCI/NH$_3$) m/e 244 (M+H)$^+$.

EXAMPLE 7B

Boc-L-(4-Thiazolyl)-Ala Amide of (2S, 3R, 4S)-2-Amino-1-cyclohexyl-3,4-dihydroxy-6-methylheptane To a solution of the product of Example 7A (14.25 g, 58.5 mmol), N-Boc-L-(4-Thiazolyl)Alanine (17.45 g, 64.4 mmol), and 1-hydroxybenzotriazole hydrate (HOBT) (9.86 g, 64.4 mmol) dissolved in dimethylformamide (DMF) (33 mL) and cooled to 0°–5° C. in an ice bath was added dropwise over 30 minutes, a solution of 1,3-dicyclohexylcarbodiimide (DCC) (14.5 g, 70.3 mmol) dissolved in DMF (27 mL). After one hour, the reaction mixture was allowed to warm to room temperature and stirred for 24 hours. The reaction was quenched by the addition of citric acid (1.14 g, 6.0 mmol) and ethanol (1.31 mL, 1.05 g, 22.0 mmol). The mixture was stirred for 1 hour and then ethyl acetate was added (285 mL). After an additional 30 minutes, the solid by-product was removed by filtration and washed with ethyl acetate (48 mL). Additional ethyl acetate (1.9 L) was added and the organic phase was washed with 1% sodium chloride (713 mL), 5% citric acid containing 1% sodium chloride (2×713 mL), 8% sodium bicarbonate (2×713 mL) and 20% sodium chloride (2×713 mL) and concentrated under reduced pressure to afford an off-white solid. The solid was dissolved in isopropanol (200 mL) with warming, treated with decolorizing carbon at 50° C. for one hour, and filtered through Celite. The filtrate was diluted with isopropanol (50 mL) and stirred at room temperature with a mechanical stirrer for 15 hours. The solid suspension was cooled to 0°–5° C. with an ice bath and stirred at this temperature for 3 hours. The solid was removed by cold filtration, washed with cold 1:1 isopropanol/heptane (100 mL), and dried in a vacuum oven at 50° C. for 48 hours to afford the title compound as a white solid in 85% yield. m.p. 156°–158° C. MS (DCI/NH$_3$) m/e 498 (M+H)$^+$.

EXAMPLE 7C

H-L-(4-Thiazolyl)Ala Amide of (2S, 3R, 4S)-2-Amino-1-cyclohexyl-3,4-dihydroxy-6-methylheptane A 12% solution of the product of Example 7B at 15°–25° C. in 3N aqueous hydrochloric acid was prepared. After 4 hours at 15°–25° C., the reaction mixture was quenched by pouring it into a mixture of 4% sodium hydroxide/15% sodium chloride/ethyl acetate. The pH of the mixture was brought up to 10–12 by the addition of 10% sodium hydroxide. The layers were separated and the aqueous layer extracted with ethyl acetate (2×). The combined organic extracts were washed with 25% sodium chloride (2×), dried over magnesium sulfate, treated with activated carbon at 50° C. for 1 hour, and filtered through Celite. The filtrate was concentrated to a solid under reduced pressure at 45° C. The solid was crystallized by dissolving in a minimum amount of ethyl acetate (5× by weight) and triturating with heptane until the ratio of ethyl acetate to heptane was 30/70 (w/w). The solution was cooled to 0°–5° C. and stirred for two hours and then filtered. The solid was dried in a vacuum oven at 45° C. for 60 hours or until the loss on dryng was less than 0.1%. The title compound was obtained as a white crystalline solid in 70–82% yield. m.p. 109°–112° C. MS (DCI/NH$_3$) m/e 398 (M+H)$^+$.

EXAMPLE 7D (2S)-2-Benzyl-3-(1-methylpiperazin-4-ylsulfonyl) propionyl-L-( 4-Thiazolyl)Ala Amide of (2S, 3R, 4S)-2-Amino-1-cyclohexyl- 3,4-dihydroxy-6-methylheptane The product of Example 7C (3.00 g, 7.6 mmol), the product of Example 4C, 2S-benzyl-3-(1-methylpiperazin-4-yl sulfonyl)propionic acid, (2.59 g, 7.9 mmol), and HOBT (1.27 g, 8.3 mmol) were dissolved in DMF (30 mL). After stirring at room temperature for 1 hour, the reaction mixture was cooled to 0°–5° C. in an ice bath and treated with the dropwise addition over a 30 minute period of a solution of DCC (1.72 g, 8.3 mmol) dissolved in DMF (8 mL). After 1 hour, the reaction mixture was allowed to warm to ambient temperature and stirred for 24 hours. The reaction mixture was quenched with citric acid (0.15 g, 0.26 mmol) and ethanol (0.17 mL, 3.04 mmol) and stirred for 1 hour. Ethyl acetate (60 mL) was added and the mixture was stirred for an additional hour. The by-product was removed by filtration and washed with ethyl acetate (10 mL). The filtrate was diluted with ethyl acetate (400 mL) and washed with 5% sodium bicarbonate solution (2×100 mL), 1% sodium chloride solution (100 mL), and 20% sodium chloride solution (100 mL). The solvent was removed under reduced pressure to afford an off-white solid. The solid was dissolved in isopropanol (80 mL) with warming, treated with decolorizing carbon at 55° C. for 1 hour, filtered through Celite, and stirred at ambient temperature with a mechanical stirrer for 12 hours. The white solid suspension was cooled to 0°–5° C. in an ice bath for 3 hours and filtered cold. The solid obtained was washed with cold 1:1 heptane/isopropanol (25 mL) and dried in a vacuum oven at 55° C. for 48 hours to afford the title comound (4.32 g, 81%) as a white solid. m.p. 169°–170° C. MS (DCI/NH$_3$) m/e 706 (M+H)$^+$.

EXAMPLE 8

N-(4-Morpholinylsulfonyl)-(L)-phenylalanyl-(L)- (2-amino-4-thiazolyl)alanyl amide of (2S, 3R, 4S)-2-Amino-1-cyclohexyl- 3,4-dihydroxy-6-methylheptane The title compound can be prepared according to the procedure disclosed in European Patent Application No. EP 399556, published Nov. 28, 1990.

EXAMPLE 9

(S)-α-[(S)-α-[(t-Butylsulfonyl)methyl] hydrocinnamide]-N-[( 1R, 2S, 3R)-1-cyclohexylmethyl-3-cyclopropyl-2,3- dihydroxypropyl]imidazol- 4-ylpropionamide The title compound can be prepared according to the procedure disclosed in European Patent Application No. EP332008, published Sep. 13, 1989.

EXAMPLE 10

(2S)-2-Benzyl-3-(1-methyl-piperazin- 4-ylsulfonyl)propionyl-(L)-(4-Thiazolyl)Ala Amide of (2S, 3R, 4S)-2-Amino-1-cyclohexyl-3,4-dihydroxy- 6-methylheptane hydrochloride salt Acetyl chloride (3.27 g, 41.65 mmol) was added to ethanol (150 ml) at 5° C. The mixture was stirred for two hours at 5° C. and added to a suspension of the product of Example 1R (30 g, 42.5 mmol) in ethanol (150 ml) at 5° C. After 2 hours, the mixture was filtered and the solvent removed under vacuum. The residue was dissolved in methylene chloride (300 ml) and the desired product was precipitated by the addition of either 3:1 heptane/ethyl acetate (1500 ml) or diethyl ether (1500 ml) or methyl t-butyl ether (1500 ml). Anal calcd for C$_{35}$H$_{56}$N$_5$O$_6$S$_2$Cl·0.5 H$_2$O: C, 55.94; H, 7.65; N, 9.32; Cl, 4.72; S, 8.53. Found: C, 56.06; H, 7.58; N, 9.30; Cl, 4.95; S, 8.17.

EXAMPLE 11

| Tablet Composition No. 5–7 | | | |
|---|---|---|---|
| Tablet Strength (as mg of compound I base) | 5 | 25 | 125 |
| COMPONENT | MG PER TABLET | | |
| Compound I (HCl salt) | 5.3 | 26.3 | 131.4 |
| Microcrystalline cellulose (Avicel ®) | 99.5 | 105.0 | 314.0 |
| Citric acid, USP, anhydrous | 4.0 | 7.5 | 22.8 |
| Crospovidone, NF | 4.6 | 5.0 | 14.0 |
| Croscarmellose sodium, NF | 4.6 | 5.0 | 14.0 |
| Povidone, NF, K-30 | 6.0 | n/a | n/a |
| Magnesium stearate, (impalpable powder, NF) | 1.0 | 1.2 | 3.8 |
| Tablet weight (mg) | 125.0 | 150.0 | 500.0 |

PROCESS FOR PREPARING THE ABOVE TABLET FORMULATIONS

The tablet compositions shown above can be prepared according to the following illustrative example based on the 25 mg strength tablet.

To prepare 10,000 tablets of 25 mg strength:
1. Compound I/HCl salt (263 grams) was mixed with Avicel® (approximately 300 grams) and screened through a 30 mesh screen.
2. Avicel® (approximately 800 grams) was screen through a 30 mesh screen and mixed with the mixture of step 1.
3. Citric acid (30 grams) was screened throught a 30 mesh screen and mixed with the mixture of step 3.

4. Crospovidone and croscarmellose (25 grams of each) were screened through a 30 mesh screen and mixed with the mixture of step 3.
5. NOTE: For the 5 mg tablet only, the povidone was screened through a 30 mesh screen and blended with the mixture of step 4.
6. The powder blend from step 4 (25 mg and 125 mg tablets) or step 5 (5 mg tablets) was blended for 2 to 4 minutes in a Hobart mixer or equivalent planetary mixer.
7. The blend from step 6 was granulated with distilled water (approximately 30 to 40 ml per 100 grams of granulation). The water was added over 5 to 10 minutes and mixing was continued for another 2 to 4 minutes.
8. The granulation was transferred to paper lined trays and dried in an oven at 60° C. until the moisture level was less than 2.5%.
9. The granules were hand-screened through a 20 mesh screen.
10. Citric acid (45 grams), crospovidone (25 grams) and croscarmellose (25 grams) were hand-screened through a 30 mesh screen.
11. The granules from step 9 and the screened materials from step 10 were transferred to a V-blender or equivalent equipment and blended for about 10 minutes.
12. Magnesium stearate (12 grams) was mixed with a portion (approximately 50 to 100 grams) of the blend from step 11 and then screened through a 20 mesh screen.
13. The mixture from step 12 is blended with the mixture from step 11 in a V-blender or equivalent equipment for approximately 4 minutes.
14. The blend from step 13 is compressed into tablets in a rotary press. Tablet weights are adjusted according to the formula (e.g., 150 mg total weight for a 25 mg tablet).

EXAMPLE 12

Bioavailability Comparisons

The following compositions comprising compound I were prepared and the bioavailability of each composition was determined in fasted dogs.

Composition S1

A composition comprising the dihydrochloride salt of compound I (115.9 mg), Avicel® (300.0 mg), crospovidone (47.6 mg), sodium starch glycolate (47.6 mg) and magnesium stearate (5.0 mg) was tabletted.

Composition S2

A composition comprising the dihydrochloride salt of compound I (115.9 mg), Avicel® (500.0 mg), crospovidone (195.2 mg), sodium starch glycolate (195.2 mg) and magnesium stearate (10.0 mg) was tabletted.

Composition S3

A composition comprising the dihydrochloride salt of compound I (110.4 mg), PEG 1450 (100 mg), Avicel (100 mg) and lactose (100 mg) was filled in capsules (hard shell gelatin capsules, gray, #000 for human use).

Composition S4

A composition comprising the monomethanesulfonate salt of compound I (120.3 mg), Avicel (250 mg), crospovidone (150 mg) and magnesium stearate (2.5 mg) was tabletted.

Composition S5

A composition comprising the dimethanesulfonate salt of compound I (120.5 mg), Avicel (150 mg) and lactose (150 mg) was filled in capsules (hard shell gelatin capsules, gray, #000 for human use).

Protocol For Oral Bioavailability Studies

Dogs (beagle dogs, mixed sexes, weighing about 10 kg) were fasted for at least 12 hours before dosing. Food was returned after the last blood sample was collected (24 hours). Water was available at all times.

A dose equivalent to 50 or 100 milligrams of compound I was administered by mouth to each dog, followed with either 20 or 50 ml of water through a feeding tube.

Blood samples were collected at the following times: 0, 0.5, 1, 2, 3, 4, 6, 8, 12 and 24 hours. Blood samples of 3 ml volume were anti-coagulated with EDTA. The plasma was separated by centrifugation and frozen until analyzed. Blood plasma concentrations of compound I were determined by HPLC.

Bioavailability was calculated as follows: % Bioavailability= [(AUC)oral×D/(AUC) intravenous]×100. (AUC)oral and (AUC) intravenous are the areas under the curve for the plasma concentration-time profiles following oral and intravenous administration, respectively. D is defined as the intravenous vs. oral DOSE ratio. In particular, D= (DOSE)iv/DOSE)oral. The intravenous dose was 3.0 mg/kg and oral dose was about 5.0 mg/kg or about 10.0 mg/kg. The (AUC) intravenous value used corresponds to the mean value from a separate group of 6 dogs. The bioavailability and Cmax (maximum concentration) data for Compositions 1–3 and S1–S5 are shown in Table 1.

TABLE 1

| Composition No. | No. of Dogs | Mean % Bioavailability | Mean Cmax µg/ml |
|---|---|---|---|
| 1 (Ex. 1A) | 8 | 69.8 | 2.45 |
| 2 (Ex. 1B) | 8 | 44.0 | 1.76 |
| 3 (Ex. 1C) | 12 | 71.1 | 4.17 |
| 4 (Ex. 1D) | 8 | 72.4 | 2.6 |
| S1 | 6 | 44.0 | 2.7 |
| S2 | 6 | 31.0 | 1.2 |
| S3 | 8 | 18.0 | 1.3 |
| S4 | 8 | 9.2 | 0.8 |
| S5 | 8 | 35.0 | 1.5 |

This data indicates that compound I is as much as 7.8 times more bioavailable when administered orally as a tablet comprising a pharmaceutically acceptable organic polycarboxylic acid as compared to a tablet or powder filled capsule composition without the organic polycarboxylic acid.

The compounds of formula II are inhibitors of renin and possess an excellent degree of activity and specificity in treating hypertension in a human or other mammal. The novel compounds of the present invention are also useful for treating congestive heart failure in a human or other mammal. The compounds of formula II are also useful for treating vascular abnormalities in a human or other mammal, especially those vascular diseases associated with diabetes, such as diabetic nephropathy, diabetic neuropathy and diabetic retinopathy. The compounds of formula II are also useful for the treatment of renal diseases in a human or other mammal, in particular acute and chronic renal failure. The compounds of formula II are also useful for the treatment of psoriasis in a human or other mammal.

Total daily dose of a compound of formula II administered to a human or other mammal in single or divided doses may be in amounts, for example, from 0.001 to 10 mg/kg body weight daily and more usually 0.01 to 10 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The foregoing is merely illustrative of the invention and is not intended to limit the invention to the disclosed compounds, methods and compositions. Variations and changes which are obvious to one skilled in the art are intended to be within the scope and nature of the invention which are defined in the appended claims.

What is claimed is:

1. A pharmaceutical composition comprising from about 20 weight % to about 30 weight % of a compound of the formula:

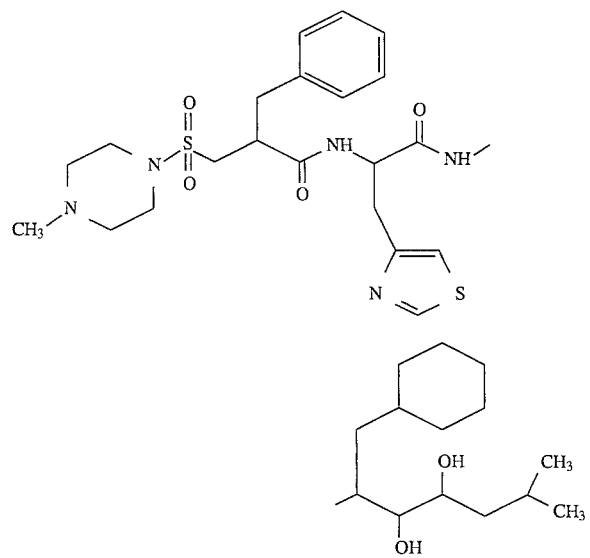

or a pharmaceutically acceptable salt thereof, from about 4 weight % to about 14 weight % of a pharmaceutically acceptable organic polycarboxylic acid and from about 40 weight % to about 80 weight % of a filler.

2. The composition of claim 1 wherein the organic polycarboxylic acid is citric acid and the filler is microcrystalline cellulose.

3. The composition of claim 1 further comprising from about 0 weight % to about 10 weight % of a pharmaceutically acceptable non-ionic surfactant.

4. A pharmaceutical composition comprising from about 20 weight % to about 30 weight % of a compound of the formula:

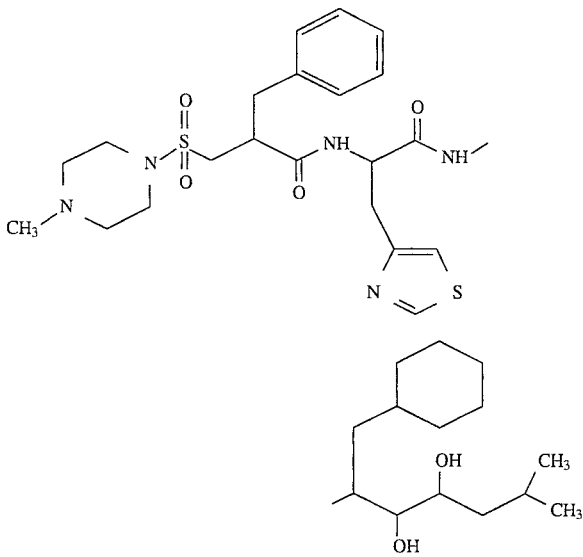

or a pharmaceutically acceptable salt thereof and from about 4 weight % to about 14 weight % of a pharmaceutically acceptable organic polycarboxylic acid.

5. The composition of claim 4 wherein the organic polycarboxylic acid is citric acid.

6. A pharmaceutical composition comprising from about 20 weight % to about 30 weight % of a compound of the formula:

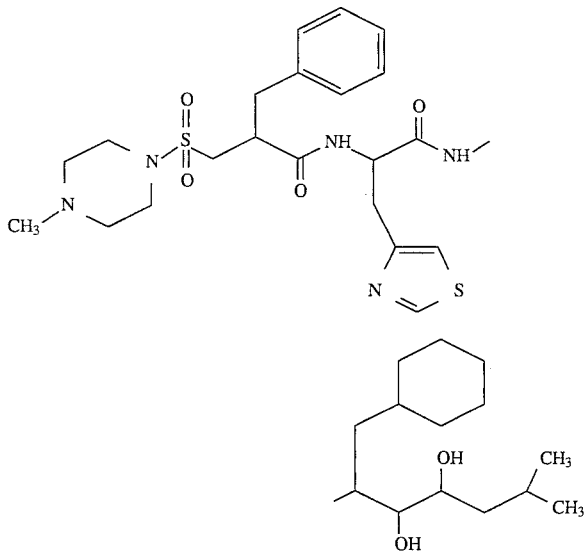

or a pharmaceutically acceptable salt thereof, from about 4 weight % to about 14 weight % of citric acid, from about 40 weight % to about 80 weight % of microcrystalline cellulose and from about 2 weight % to about 11 weight % of crospovidone.

* * * * *